US008329995B2

(12) United States Patent
Facciotti et al.

(10) Patent No.: US 8,329,995 B2
(45) Date of Patent: Dec. 11, 2012

(54) SOYBEANS WITH REDUCED ISOFLAVONES

(75) Inventors: Daniel Facciotti, Davis, CA (US); Ann J. Slade, Bellevue, WA (US)

(73) Assignee: Arcadia Biosciences, Inc., Davis, CA (US)

(*) Notice: Subject to any disclaimer, the term of this patent is extended or adjusted under 35 U.S.C. 154(b) by 250 days.

(21) Appl. No.: 12/668,008

(22) PCT Filed: Jul. 3, 2008

(86) PCT No.: PCT/US2008/069258
§ 371 (c)(1),
(2), (4) Date: Jan. 6, 2010

(87) PCT Pub. No.: WO2009/009450
PCT Pub. Date: Jan. 15, 2009

(65) Prior Publication Data
US 2010/0196582 A1 Aug. 5, 2010

Related U.S. Application Data

(60) Provisional application No. 60/958,640, filed on Jul. 6, 2007, provisional application No. 61/133,301, filed on Jun. 26, 2008.

(51) Int. Cl.
*A01H 5/00* (2006.01)
*A01H 5/10* (2006.01)
*A01H 4/00* (2006.01)
(52) U.S. Cl. .......................... 800/298; 800/312; 800/295
(58) Field of Classification Search ........................ None
See application file for complete search history.

(56) References Cited

U.S. PATENT DOCUMENTS

| 4,684,612 | A | * | 8/1987 | Hemphill et al. | ............. | 435/426 |
| 5,994,075 | A | | 11/1999 | Goodfellow | | |
| 6,521,433 | B1 | | 2/2003 | Fader | | |
| 7,098,011 | B1 | | 8/2006 | Fader et al. | | |
| 2004/0053236 | A1 | | 3/2004 | McCallum et al. | | |
| 2005/0289669 | A1 | * | 12/2005 | Wan et al. | ...................... | 800/282 |
| 2006/0005276 | A1 | * | 1/2006 | Falco et al. | ...................... | 800/281 |
| 2006/0242735 | A1 | * | 10/2006 | Fader et al. | ................... | 800/284 |
| 2007/0118920 | A1 | | 5/2007 | Leon et al. | | |

OTHER PUBLICATIONS

International Preliminary Report on Patentability for PCT/US2008/069258, Jan. 12, 2010.
Written Opinion of the international Searching Authority for PCT/US2008/069258, Jun. 29, 2009.
Young, Soy protein in relation to human protein and amino acid nutrition, J. Am. Diet Assoc. 91(7):828-835, 1991.
Setchell et al., Isoflavone content of infant formulas and the metabolic fate of these phytoestrogens in early life. Am. J. Clin. Nutt. 68(suppl):1453S, 1998.
Yellayi et al., the phytoestrogen genistein induces thymic and immune changes: A human health concern? Proc. Natl. Acad. Sci. U.S.A. 99:7616-7621, 2002.
Paediatric Group, British Dietetic Association, Paediatric Group csition statement on the use of soya protein for infants.
Paediatric Policy Soy Protein Formula, Royal Australian College of Phyysicians, 2006.
Humphreys and Chapple, Molecular 'pharming' with plant P450s Trends in Plant Science, 5(7)271-272 2000.
Yu et al., Production of the isoflavones enistein and daidzein in non-legume dicot and monocot tissues. Plant Physiol., 124:761-793, 2000.
Jung et al., Identification and expression of isoflavone synthase, the key enzyme for iosynthesis of iso fiavones in legumes. Nature Biotechnology 18:208-212, 2000.
Subramanian et al., RNA interference of soybean isollavone synthase genes leads to silencing in tissues distal to the transformation site and to enhanced susceptibility to Phytophthora sojae. Plant Physiol, 137(4):1345-1353, 2005.
GenBank Accession No. AF195798, 2000.
GenBank Accession No. AF195819, 2000.
NCBI Accession No. AAF34519, 2000.
NCBI Accession No. AAF45143, 2000.
Horiguchi, RNA silencing in plants: a shortcut to functional analysis. Differentiation 72(2-3);65-73, 2004.
Hamilton and Baulcombe, A species of small antisense RNA in posttranscriptional gene silencing in plants. Science 286(5441):886, 1999.
Matzke et al, RNA: guiding gene silencing. Science 293(5532)1080-3, 2001.
McCallum et al., Targeting Induced Local Lesions IN Genomics (TILLING) for Plant Functional Genomics, Plant Physiology 123:439-442, 2000.
McCallum et al., Targeted screening for induced mutations. Nature Biotechnology 18:455-457 2000.
Chen and Ronald, A rapid DNA minipreparation method suitable for AFLP and other PCR applications. Plant Molecular Biology Reporter. 17(1):53-57, 2004.
Stewart and Via, A rapid CTAB DNA isolation technique useful for RAPD fingerprinting and other PCR applications. Biotechniques 14(5):7480750, 1993.
Innis et al, (Eds), PCR Protocols: A guide to methods and applications. Academic Press, Inc. 1990.
Li et al., Integrated platform for detection of DNA sequence variants using capillary array electrophoresis. Electrophoresis. May 2002;23(10):1499-511.
Colbert et al., High-throughput screening for induced point mutations. Plant Physiology 126:480-484, 2001.
Ng and Henikoff, SIFT: predicting amino acid changes that affect protein function, Nucleic Acids Research 31 (13):3812-3814, 2003.
Henikoff and Henikoff, Using substitution probabilities to improve position-specific scoring matrices. Comput Appl Biosci. Apr. ;12(2):135-43, 1996.

(Continued)

*Primary Examiner* — Brent T Page
*Assistant Examiner* — Lee A Visone

(57) ABSTRACT

Non-naturally occurring soybean plants and seeds having reduced isoflavones are provided. A series of independent non-transgenic human-induced mutations found in one or more isoflavone synthase genes of soybean; soybean plants having these mutations in one or more isoflavone synthase genes; and a method of creating and finding similar and/or additional mutations of the isoflavone synthase gene by screening pooled and/or individual DNA of soybean plants. The results are soybean plants and seeds having reduced isoflavones.

12 Claims, 6 Drawing Sheets

OTHER PUBLICATIONS

Taylor and Greene, PARSESNP: a tool for the analysis of nucleotide polyrtmorphisms. Nucleic: Acids Research 31 (13):3808-3811, 2003.

Thomas et al., Quantitative analysis of the principle soy isoflavones genistein, daidzein and glycitein, and their primary conjugated metabolites in human plasma and urine using reversed-phase high-performance liquid chromatography with ultraviolet detection. J Chromatogr B Biomed Sci Appl 760:191-205, 2001.

Kirakosyan et al., Isoflavone levels in five soybean (Glycine max) genotypes are altered by phytochrome-mediated light treatments. J Agric Food Chem. Jan. 11;54(1):54-8, 2006.

Shimada et al., Genome-wide analyses of the structural gene famines involved in the legume-specific 5-deoxyisoflavonoid biosynthesis of Lotus japonicus. DNA Research 14:25-36, 2007.

* cited by examiner

Allelic mutation series for IFS1 and IFS2

Gene: IFS1

|  | Nucleotide Change[1] | Effect[2] | Mutation[3] | Homozygous or Heterozygous |
|---|---|---|---|---|
| Fragment A | C190T | L42F | S. Missense | Het |
|  | C208T | L48F | S. Missense | Homo |
|  | C211T | H49Y | S. Missense | Homo |
|  | C242T | A59V | S. Missense | Homo |
|  | C403T | L113F | S. Missense | Homo |
|  | T436C | F124L | S. Missense | Homo |
|  | T448A | W128R | S. Missense | Het |
|  | G450A | W128* | STOP | Homo |
|  | A464T | K133M | S. Missense | Homo |
|  | C466T | L134F | S. Missense | Het |
|  | G478A | D138N | S. Missense | Homo |
|  | C497T | T144I | S. Missense | Het |
|  | C514T | P150S | S. Missense | Het |
|  | G600C | E178D | S. Missense | Het |

Gene: IFS2

|  | Nucleotide Change[1] | Effect[2] | Mutation[3] | Homozygous or Heterozygous |
|---|---|---|---|---|
| Fragment A | G139T | R30C | S. Missense | Het |
|  | A341T | E97V | S. Missense | Het |
|  | A244? | Frameshift | STOP | Het |
|  | C427T | P126S | S. Missense | Het |
|  | G463A | D138N | S. Missense | Het |
|  | G525T | K158N | S. Missense | Het |
| Fragment B | T539C | M163T | S. Missense | Het |
|  | G637A | E196K | S. Missense | Het |
|  | G640A | E197K | S. Missense | Het |
|  | G661A | E204K | S. Missense | Het |
|  | C691T | L214F | S. Missense | Het |
|  | A725T | K225M | S. Missense | Het |
|  | A757T | I236F | S. Missense | Het |
|  | C776T | P242L | S. Missense | Het |
|  | A823T | R*258 | STOP | Het |
|  | G938A | G296D | S. Missense | Het |
| Fragment C | G1106A | D307N | S. Missense | Het |
|  | G1115A | A310A | S. Missense | Het |
|  | G1118A | V311M | S. Missense | Het |
|  | G1132A | W*315 | STOP | Het |
|  | G1139A | A318T | S. Missense | Het |
|  | C1145T | L320F | S. Missense | Het |
|  | C1157T | P324S | S. Missense | Het |
|  | C1214T | L343F | S. Missense | Het |
|  | C1244T | P353S | S. Missense | Het |
|  | C1286T | P367S | S. Missense | Het |

MUTATION Key:
[1] G600C = Guanine at DNA base 600 (wild-type) converted to Cytosine (mutant)
[2] E178D = Glutamic Acid codon at amino acid position 178 converted to Aspartic Acid codon
[3] S. Missense = Severe Missense mutation, STOP = Nonsense mutation Table showing the allelic series of mutations found in IFS1 and IFS2 through the use of TILLING® technology. Note all mutations recovered for IFS2 are Heterozygous whereas IFS1 gives the expected proportion of Heterozygous and Homozygous individuals.

FIG. 2

Figure showing different number of loci for IFS1 vs. IFS2 using qPCR cycle number.

RNA expression levels determined with RT PCR for Wild Type and mutant alleles for IFS1 and IFS2 in cotyledons and seed axis for Wild Type and Double Mutant (W128* / K158N) homozygous plants.

Graph showing the levels of individual and total isoflavones in mutant and WT seed shown as a percentage of Wild Type.

SEQUENCE LISTING

<160> NUMBER OF SEQ ID NOS: 12

<210> SEQ ID NO 1
<211> LENGTH: 1774
<212> TYPE: DNA
<213> ORGANISM: Glycine max

<400> SEQUENCE: 1

```
gtaattaacc tcactcaaac tcgggatcac agaaaccaac aacagttctt gcactgaggt      60
ttcacgatgt tgctggaact tgcacttggt ttgtttgtgt tagctttgtt tctgcacttg     120
cgtcccacac caagtgcaaa atcaaaagca cttcgccacc tcccaaaccc tccaagccca     180
```

```
aagcctcgtc ttcccttcat tggccacctt cacctcttaa aagataaact tctccactat    240
gcactcatcg atctctccaa aaagcatggc cccttattct ctctctcctt cggctccatg    300
ccaaccgtcg ttgcctccac ccctgagttg ttcaagctct tcctccaaac ccacgaggca    360
acttccttca acacaaggtt ccaaacctct gccataagac gcctcactta cgacaactct    420
gtggccatgg ttccattcgg accttactgg aagttcgtga ggaagctcat catgaacgac    480
cttctcaacg ccaccaccgt caacaagctc aggcctttga ggacccaaca gatccgcaag    540
ttccttaggg ttatggccca aagcgcagag gcccagaagc cccttgacgt caccgaggag    600
cttctcaaat ggaccaacag caccatctcc atgatgatgc tcggcgaggc tgaggagatc    660
agagacatcg ctcgcgaggt tcttaagatc ttcggcgaat acagcctcac tgacttcatc    720 tggccttttga agtatctcaa ggttggaaag tatgagaaga ggattgatga catcttgaac    780
aagttcgacc ctgtcgttga aagggtcatc aagaagcgcc gtgagatcgt cagaaggaga    840
aagaacggag aagttgttga gggcgaggcc agcggcgtct tcctcgacac tttgcttgaa    900
ttcgctgagg acgagaccat ggagatcaaa attaccaagg agcaaatcaa gggccttgtt    960
gtcgactttt tctctgcagg gacagattcc acagcggtgg caacagagtg ggcattggca   1020
gagctcatca acaatcccag ggtgttgcaa aaggctcgtg aggaggtcta cagtgttgtg   1080
ggcaaagata gactcgttga cgaagttgac actcaaaacc ttccttacat tagggccatt   1140
gtgaaggaga cattccgaat gcacccacca ctcccagtgg tcaaaagaaa gtgcacagaa   1200
gagtgtgaga ttaatgggta tgtgatccca gagggagcat tggttctttt caatgtttgg   1260
caagtaggaa gggaccccaa atactgggac agaccatcag aattccgtcc cgagaggttc   1320
ttagaaactg gtgctgaagg ggaagcaggg cctcttgatc ttaggggcca gcatttccaa   1380
ctcctcccat ttgggtctgg gaggagaatg tgccctggtg tcaatttggc tacttcagga   1440
atggcaacac ttcttgcatc tcttatccaa tgctttgacc tgcaagtgct gggccctcaa   1500
ggacaaatat tgaaaggtga tgatgccaaa gttagcatgg aagagagagc tggcctcaca   1560
gttccaaggg cacatagtct cgtttgtgtt ccacttgcaa ggatcggcgt tgcatctaaa   1620 ctccttttctt aattaagata atcatcatat acaatagtag tgtcttgcca tcgcagttgc   1680
tttttatgta ttcataatca tcatttcaat aaggtgtgac tggtacttaa tcaagtaatt   1740
aaggttacat acatgcaaaa aaaaaaaaaa aaaa                                1774

<210> SEQ ID NO 2
<211> LENGTH: 1902
<212> TYPE: DNA
<213> ORGANISM: Glycine max

<400> SEQUENCE: 2
aaaattagcc tcacaaaagc aaagatcaaa caaaccaagg acgagaacac gatgttgctt     60
gaacttgcac ttggtttatt ggttttggct ctgtttctgc acttgcgtcc cacacccact    120
gcaaaatcaa aagcacttcg ccatctccca aacccaccaa gcccaaagcc tcgtcttccc    180
ttcataggac accttcatct cttaaaagac aaacttctcc actacgcact catcgacctc    240
tccaaaaaac atggtccctt attctctctc tactttggct ccatgccaac cgttgttgcc    300
tccacaccag aattgttcaa gctcttcctc caaacgcacg aggcaacttc cttcaacaca    360
aggttccaaa cctcagccat aagacgcctc acctatgata gctcagtggc catggttccc    420 ttcggaccttt actggaagtt cgtgaggaag ctcatcatga cgaccttccc caacgccacc    480
actgtaaaca gttgaggcc tttgaggacc caacagaccc gcaagttcct tagggttatg    540
```

```
gcccaaggcg cagaggcaca gaagcccctt gacttgaccg aggagcttct gaaatggacc      600
aacagcacca tctccatgat gatgctcggc gaggctgagg agatcagaga catcgctcgc      660
gaggttctta agatctttgg cgaatacagc ctcactgact tcatctggcc attgaagcat      720
ctcaaggttg aaagtatga aagaggatc gacgacatct gaacaagtt cgaccctgtc         780 gttgaaaggg tcatcaagaa gcgccgtgag atcgtgagga ggagaaagaa cggagaggtt      840
gttgagggtg aggtcagcgg ggttttcctt gacactttgc ttgaattcgc tgaggatgag      900
accatggaga tcaaaatcac caaggaccac atcgagggtc ttgttgtcgt gagtttcctg      960
cttcattcat tgatcgaaat atgcagtatt ttgttaacaa gagatcgaga attgacattt     1020
atatattcat gtggtggcaa ttaattaacg gtacgcattc ttaatcgata ttgtgtatgt     1080
gcaggacttt ttctcggcag gaacagactc cacagcggtg gcaacagagt gggcattggc     1140
agaactcatc aacaatccta aggtgttgga aaaggctcgt gaggaggtct acagtgttgt     1200
gggaaaggac agacttgtgg acgaagttga cactcaaaac cttccttaca ttagagcaat     1260
cgtgaaggag acattccgca tgcacccgcc actcccagtg gtcaaaagaa agtgcacaga     1320
agagtgtgag attaatggat atgtgatccc agagggagca ttgattctct tcaatgtatg     1380
gcaagtagga agagacccca aatactggga cagaccatcg gagttccgtc ctgagaggtt     1440
cctagagaca ggggctgaag gggaagcagg gcctcttgat cttaggggac aacattttca     1500
acttctccca tttgggtctg ggaggagaat gtgccctgga gtcaatctgg ctacttcggg     1560
aatggcaaca cttcttgcat ctcttattca gtgcttcgac ttgcaagtgc tgggtccaca     1620
aggacagata ttgaagggtg gtgacgccaa agttagcatg gaagagagag ccggcctcac     1680
tgttccaagg gcacatagtc ttgtctgtgt tccacttgca aggatcggcg ttgcatctaa     1740
actcctttct taattaagat catcgtcatc atcatcatat ataatattta cttttttgtgt    1800 gttgataatc atcatttcaa taaggtctcg ttcatctact ttttatgaag tatataagcc     1860
cttccatgca cattgtatca tctcccattt gtcttcgttt gc                        1902
```

<210> SEQ ID NO 3
<211> LENGTH: 521
<212> TYPE: PRT
<213> ORGANISM: Glycine max

<400> SEQUENCE: 3

```
Met Leu Leu Glu Leu Ala Leu Gly Leu Phe Val Leu Ala Leu Phe Leu
  1               5                  10                  15

His Leu Arg Pro Thr Pro Ser Ala Lys Ser Lys Ala Leu Arg His Leu
             20                  25                  30

Pro Asn Pro Pro Ser Pro Lys Pro Arg Leu Pro Phe Ile Gly His Leu
         35                  40                  45

His Leu Leu Lys Asp Lys Leu Leu His Tyr Ala Leu Ile Asp Leu Ser
     50                  55                  60

Lys Lys His Gly Pro Leu Phe Ser Leu Ser Phe Gly Ser Met Pro Thr
 65                  70                  75                  80

Val Val Ala Ser Thr Pro Glu Leu Phe Lys Leu Phe Leu Gln Thr His
                 85                  90                  95

Glu Ala Thr Ser Phe Asn Thr Arg Phe Gln Thr Ser Ala Ile Arg Arg
            100                 105                 110

Leu Thr Tyr Asp Asn Ser Val Ala Met Val Pro Phe Gly Pro Tyr Trp
        115                 120                 125

Lys Phe Val Arg Lys Leu Ile Met Asn Asp Leu Leu Asn Ala Thr Thr
```

130                 135                 140
Val Asn Lys Leu Arg Pro Leu Arg Thr Gln Gln Ile Arg Lys Phe Leu
145                 150                 155                 160

Arg Val Met Ala Gln Ser Ala Glu Ala Gln Lys Pro Leu Asp Val Thr
                165                 170                 175

Glu Glu Leu Leu Lys Trp Thr Asn Ser Thr Ile Ser Met Met Met Leu
                180                 185                 190

Gly Glu Ala Glu Glu Ile Arg Asp Ile Ala Arg Glu Val Leu Lys Ile
                195                 200                 205

Phe Gly Glu Tyr Ser Leu Thr Asp Phe Ile Trp Pro Leu Lys Tyr Leu
210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Ala Ser Gly Val Phe
                260                 265                 270

Leu Asp Thr Leu Leu Glu Phe Ala Glu Asp Glu Thr Met Glu Ile Lys
                275                 280                 285

Ile Thr Lys Glu Gln Ile Lys Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Arg Val Leu Gln Lys Ala Arg Glu Glu Val Tyr Ser
                325                 330                 335

Val Val Gly Lys Asp Arg Leu Val Asp Glu Val Asp Thr Gln Asn Leu
                340                 345                 350

Pro Tyr Ile Arg Ala Ile Val Lys Glu Thr Phe Arg Met His Pro Pro
                355                 360                 365

Leu Pro Val Val Lys Arg Lys Cys Thr Glu Glu Cys Glu Ile Asn Gly
370                 375                 380

Tyr Val Ile Pro Glu Gly Ala Leu Val Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

Arg Phe Leu Glu Thr Gly Ala Glu Gly Ala Gly Pro Leu Asp Leu
                420                 425                 430

Arg Gly Gln His Phe Gln Leu Leu Pro Phe Gly Ser Gly Arg Arg Met
                435                 440                 445

Cys Pro Gly Val Asn Leu Ala Thr Ser Gly Met Ala Thr Leu Leu Ala
450                 455                 460

Ser Leu Ile Gln Cys Phe Asp Leu Gln Val Leu Gly Pro Gln Gly Gln
465                 470                 475                 480

Ile Leu Lys Gly Asp Asp Ala Lys Val Ser Met Glu Glu Arg Ala Gly
                485                 490                 495

Leu Thr Val Pro Arg Ala His Ser Leu Val Cys Val Pro Leu Ala Arg
                500                 505                 510

Ile Gly Val Ala Ser Lys Leu Leu Ser
                515                 520

<210> SEQ ID NO 4
<211> LENGTH: 521
<212> TYPE: PRT
<213> ORGANISM: Glycine max

<400> SEQUENCE: 4

Met Leu Leu Glu Leu Ala Leu Gly Leu Val Leu Ala Leu Phe Leu
1               5                   10                  15

His Leu Arg Pro Thr Pro Thr Ala Lys Ser Lys Ala Leu Arg His Leu
        20                  25                  30

Pro Asn Pro Pro Ser Pro Lys Pro Arg Leu Pro Phe Ile Gly His Leu
            35                  40                  45

His Leu Leu Lys Asp Lys Leu Leu His Tyr Ala Leu Ile Asp Leu Ser
50                  55                  60

Lys Lys His Gly Pro Leu Phe Ser Leu Tyr Phe Gly Ser Met Pro Thr
65                  70                  75                  80

Val Val Ala Ser Thr Pro Glu Leu Phe Lys Leu Phe Leu Gln Thr His
                85                  90                  95

Glu Ala Thr Ser Phe Asn Thr Arg Phe Gln Thr Ser Ala Ile Arg Arg
            100                 105                 110

Leu Thr Tyr Asp Ser Ser Val Ala Met Val Pro Phe Gly Pro Tyr Trp
        115                 120                 125

Lys Phe Val Arg Lys Leu Ile Met Asn Asp Leu Pro Asn Ala Thr Thr
130                 135                 140

Val Asn Lys Leu Arg Pro Leu Arg Thr Gln Gln Thr Arg Lys Phe Leu
145                 150                 155                 160

Arg Val Met Ala Gln Gly Ala Glu Ala Gln Lys Pro Leu Asp Leu Thr
                165                 170                 175

Glu Glu Leu Leu Lys Trp Thr Asn Ser Thr Ile Ser Met Met Met Leu
            180                 185                 190

Gly Glu Ala Glu Glu Ile Arg Asp Ile Ala Arg Glu Val Leu Lys Ile
        195                 200                 205

Phe Gly Glu Tyr Ser Leu Thr Asp Phe Ile Trp Pro Leu Lys His Leu
210                 215                 220

Lys Val Gly Lys Tyr Glu Lys Arg Ile Asp Asp Ile Leu Asn Lys Phe
225                 230                 235                 240

Asp Pro Val Val Glu Arg Val Ile Lys Lys Arg Arg Glu Ile Val Arg
                245                 250                 255

Arg Arg Lys Asn Gly Glu Val Val Glu Gly Glu Val Ser Gly Val Phe
            260                 265                 270

Leu Asp Thr Leu Leu Glu Phe Ala Glu Asp Glu Thr Met Glu Ile Lys
        275                 280                 285

Ile Thr Lys Asp His Ile Glu Gly Leu Val Val Asp Phe Phe Ser Ala
290                 295                 300

Gly Thr Asp Ser Thr Ala Val Ala Thr Glu Trp Ala Leu Ala Glu Leu
305                 310                 315                 320

Ile Asn Asn Pro Lys Val Leu Glu Lys Ala Arg Glu Glu Val Tyr Ser
                325                 330                 335

Val Val Gly Lys Asp Arg Leu Val Asp Glu Val Asp Thr Gln Asn Leu
            340                 345                 350

Pro Tyr Ile Arg Ala Ile Val Lys Glu Thr Phe Arg Met His Pro Pro
        355                 360                 365

Leu Pro Val Val Lys Arg Cys Thr Glu Glu Cys Glu Ile Asn Gly
370                 375                 380

Tyr Val Ile Pro Glu Gly Ala Leu Ile Leu Phe Asn Val Trp Gln Val
385                 390                 395                 400

Gly Arg Asp Pro Lys Tyr Trp Asp Arg Pro Ser Glu Phe Arg Pro Glu
                405                 410                 415

```
Arg Phe Leu Glu Thr Gly Ala Glu Gly Ala Gly Pro Leu Asp Leu
            420                 425                 430

Arg Gly Gln His Phe Gln Leu Leu Pro Phe Gly Ser Gly Arg Arg Met
        435                 440                 445

Cys Pro Gly Val Asn Leu Ala Thr Ser Gly Met Ala Thr Leu Leu Ala
450                 455                 460

Ser Leu Ile Gln Cys Phe Asp Leu Gln Val Leu Gly Pro Gln Gly Gln
465                 470                 475                 480

Ile Leu Lys Gly Gly Asp Ala Lys Val Ser Met Glu Glu Arg Ala Gly
                485                 490                 495

Leu Thr Val Pro Arg Ala His Ser Leu Val Cys Val Pro Leu Ala Arg
            500                 505                 510

Ile Gly Val Ala Ser Lys Leu Leu Ser
        515                 520

<210> SEQ ID NO 5
<211> LENGTH: 29
<212> TYPE: DNA
<213> ORGANISM: Artificial Sequence
<220> FEATURE:
<223> OTHER INFORMATION: Synthesized Construct

<400> SEQUENCE: 5
ctcgggatca cagaaaccaa caacagttc                                    29

<210> SEQ ID NO 6
<211> LENGTH: 27
<212> TYPE: DNA
<213> ORGANISM: Artificial Sequence
<220> FEATURE:
<223> OTHER INFORMATION: Synthesized Construct

<400> SEQUENCE: 6
gtccatttga gaagctcctc ggtgacg                                      27

<210> SEQ ID NO 7
<211> LENGTH: 30
<212> TYPE: DNA
<213> ORGANISM: Artificial Sequence
<220> FEATURE:
<223> OTHER INFORMATION: Synthesized Construct

<400> SEQUENCE: 7
cctcacaaaa gcaaagatca aacaaaccaa                                   30

<210> SEQ ID NO 8
<211> LENGTH: 29
<212> TYPE: DNA
<213> ORGANISM: Artificial Sequence
<220> FEATURE:
<223> OTHER INFORMATION: Synthesized Construct

<400> SEQUENCE: 8
catttcagaa gctcctcggt caagtcaag                                    29

<210> SEQ ID NO 9
<211> LENGTH: 27
<212> TYPE: DNA
<213> ORGANISM: Artificial Sequence
<220> FEATURE:
<223> OTHER INFORMATION: Synthesized Construct

<400> SEQUENCE: 9
cttcccaacg ccaccactgt aaacaag                                      27
```

```
<210> SEQ ID NO 10
<211> LENGTH: 30
<212> TYPE: DNA
<213> ORGANISM: Artificial Sequence
<220> FEATURE:
<223> OTHER INFORMATION: Synthesized Construct

<400> SEQUENCE: 10
cgtaccgtta attaattgcc accacatgaa                                          30

<210> SEQ ID NO 11
<211> LENGTH: 30
<212> TYPE: DNA
<213> ORGANISM: Artificial Sequence
<220> FEATURE:
<223> OTHER INFORMATION: Synthesized Construct

<400> SEQUENCE: 11
atggagatca aaatcaccaa ggaccacatc                                          30

<210> SEQ ID NO 12
<211> LENGTH: 30
<212> TYPE: DNA
<213> ORGANISM: Artificial Sequence
<220> FEATURE:
<223> OTHER INFORMATION: Synthesized Construct

<400> SEQUENCE: 12
tgtctctagg aacctctcag gacggaactc                                          30
```

SOYBEANS WITH REDUCED ISOFLAVONES

CROSS-REFERENCE TO RELATED APPLICATIONS

This application claims priority to PCT Application No. PCT/US2008/069258, filed Jul. 3, 2008, which claims priority to U.S. Provisional Application No. 60/958,640, filed on Jul. 6, 2007 and U.S. Provisional Application No. 61/133,301, filed on Jun. 26, 2008, all of which are hereby incorporated by reference herein.

STATEMENT REGARDING FEDERALLY SPONSORED RESEARCH OR DEVELOPMENT

This invention was made with government support under National Cancer Institute SBIR Contract #HHSN261200533004C. The government has certain rights in this invention.

FIELD OF THE INVENTION

Non-naturally occurring soybean plants and seeds having reduced isoflavones are described herein. This disclosure further provides non-transgenic human-induced mutations of the isoflavone synthase genes of soybean and soybean plants having these non-transgenic mutations in their isoflavone synthase sequences. In particular, the disclosure further concerns soybean plants and seeds having reduced isoflavones as a result of non-transgenic human-induced mutations in one or more isoflavone synthase genes. Methods that utilize non-transgenic means to create soybean plants having mutations in their isoflavone synthase genes are also provided.

BACKGROUND

Soybean (*Glycine max*) provides an excellent source of dietary protein and fiber and is a good source of calcium, iron, zinc, phosphate, magnesium, B vitamins, and folate. It contains all the essential amino acids required in the human diet and, if ingested in the proper amount, soybean can replace animal protein as the sole source of dietary protein (Young, Journal of the American Dietetic Association, 91:828-36, 1991). Because of its high nutritional value, the use of soy protein in food products has increased. In addition to being eaten whole, soybean seed is a versatile food source that can be processed into multiple products including tofu, cheese, meat alternatives, textured soy protein, tempeh, and yogurt. Over the past 10 years, soy's versatility has led to the entry of more than 2,000 new soy food products into the market place (Marsh Laux, Soyfoods Industry Profile, Agricultural Marketing Resource Center, Iowa State University, January 2003). Soy is also used to make infant formula, which is now widely used in the United States. Of those infants in the United States who are fed formula, approximately twenty-five percent or 750,000 consume soy formula. It is particularly valuable for children who are lactose-intolerant or allergic to cow's milk.

Soy-protein foods, including infant formula, are high in the isoflavones genistein and daidzein and their glycosides. These phytoestrogens are nonsteroidal compounds that are similar in both structure and action to estrogen and have been associated with the prevention of menopausal symptoms and hormone-related chronic diseases, including cancer and cardiovascular disease. Though the consumption of phytoestrogens may have beneficial effects in adults, these bioactive compounds exert a wide range of both hormone-dependent and hormone-independent physiological actions and their health effects in infants, who normally have low circulating hormone levels, are not well understood.

In infants who are fed exclusively soy formula, plasma isoflavone concentrations are 13,000- to 22,000-fold higher than plasma estradiol levels early in life and the daily intake of isoflavones in soy-fed infants is five- to ten-fold higher (relative to body weight) than the level shown to affect the menstrual cycle of adult women (Setchell et al., Am J. Clin. Nutr. 68(suppl):1453S-1461S, 1998). To put these values into context, it has been suggested that children fed solely soy milk are consuming the hormonal equivalent of five birth control pills per day. Because exposure to pharmacologically active compounds such as isoflavones could have adverse developmental effects, the ingestion of soy formula by infants raises important health concerns.

Studies in rodent models have shown that significant changes to the thymus and immune system occur in mice following genistein treatment that results in plasma levels comparable to those reported in soy-fed infants (Yellayi et al., Proc. Natl. Acad. Sci. U.S.A 99:7616-7621, 2002). Consistent with these findings, both gamma globulins and immunoglobulins are decreased in soy-fed infants compared to infants who are fed cow's milk and, as a result, soy-fed infants show a higher prevalence of asthma and allergies. Additionally, women who were fed soy products as infants show a 90% increase in the regular use of allergy medicine suggesting that there may be long-term consequences to soy ingestion early in life. In addition to affecting immune function, isoflavones, in particular genistein, inhibit thyroid peroxidase, the enzyme which makes the hormones T3 and T4, and isoflavones can disrupt thyroid function, causing hypothyroidism and goiter. The observation that infants who ingest soy products are at increased risk for developing autoimmune thyroid disease suggests that exposure to high levels of isoflavones in early life may affect the development of autoimmune diseases.

Estrogen exposure during critical stages of development disrupts reproductive and endocrine systems raising concerns that estrogenic actions of soy isoflavones may have similar long-term adverse effects in infants. During development, extreme changes in estrogen levels cause long-term changes in the reproductive organs of both males and females. Upon sexual maturation, men exhibit smaller testes than normal. In females, premature maturation is a consequence causing both physiological and psychological difficulties. Further, later in life these women may experience reproductive problems such as failure to menstruate and infertility as well as increased risk of breast cancer. Findings like these have led some physicians and scientists to suggest that soy products be used with caution, particularly during infancy and early childhood. In 2003, the Paediatric Group of the British Dietetic Association recommended that dieticians discourage the use of soy protein during the first six months of life when phytoestrogens are most likely to exert developmental effects (http://www.bda.uk.com/). The Paediatric policy of the Royal Australian College of Physicians cautions against the unnecessary use of soy formula stating that there is some evidence that soy formula may impair immunity and emphasizing that the long-term effects of soy contaminants on health are unknown (http://www.racp.edu.au/hpu/paed/soy/index.htm).

Soy food products have many nutritional advantages and soy-based baby food and formula with reduced isoflavone content would limit the exposure of children to the possible harmful effects associated with phytoestrogens. This may be achieved by reducing the enzyme isoflavone synthase in the soybeans used to make formula, thereby limiting their synthesis of isoflavones. This enzyme catalyzes the conversion of liquiritigenin and naringenin to the phytoestrogens daidzein and genistein, respectively (Humphreys et al., Trends in Plant Science, 5(7); 271-272, 2000). Two genes encoding isoflavone synthases (IFS), isoflavone synthase 1 (IFS1) and isoflavone synthase 2 (IFS2), have been identified in soybean to date (Jung et al., Nature Biotechnology 18(2):208-212, 2000) and it is possible that additional genes for this enzyme exist in soybean. The reduction of isoflavones from soy would decrease some of the adverse effects that are thought to occur when isoflavone-containing soy products are ingested, especially early in life. Soy products made from soybeans with reduced phytoestrogens would provide consumers with food alternatives that may better suit their personal health needs.

Soybean lines with varying isoflavone levels have been developed using standard breeding methods. Some lines have lower levels, the isoflavone levels in the reduced lines still represent a significant amount and it would be useful to have soybean cultivars with even greater reductions in their isoflavone content.

Genetic engineering can be used to modify expression of particular genes and such techniques have been utilized successfully to increase isoflavone production in soybean (Yu et al., Plant Physiol. 124:781-793, 2000; Jung et al., Nature Biotechnology 18:208-212, 2000; WO 00/44909; U.S. Pat. No. 6,521,433; WO 03/072790 A2; US 20030150012 A1; US 20040128711; US 20040006795). However, there have been no reports to date that isoflavone content of soybean seed can be significantly reduced utilizing any method, including standard breeding, mutagenesis or transgenic technology. Subramanian et al. (Plant Physiol. 137:1345-1353, 2005) reported that isoflavone accumulation in cotyledon tissues in response to a pathogen was reduced following their transformation with an RNAi construct to silence ISF1 and ISF2. However, the transformed tissues were not grown into plants and the ability of this genetic engineering to reduce isoflavone content of soybean seeds has never been evaluated. In addition, public acceptance of genetically modified plants, particularly with respect to plants used for food, is low. Therefore, it would be useful to have novel soybean cultivars that have further reduced levels of phytoestrogens in their seeds and in particular, those having reduced levels of phytoestrogens in their seeds due to alterations in isoflavone synthases that are not the result of genetic engineering.

SUMMARY

Non-naturally occurring soybean plants, seeds, plant parts, and progeny thereof having reduced isoflavones in their seeds compared to wild type soybean plants, in particular, wherein the reduced isoflavones are caused by a non-transgenic human-induced mutation in one or more isoflavone synthase genes, are described herein.

In one aspect, the non-naturally occurring soybean plant produces seeds having an isoflavone level reduced as compared to a wild type plant, wherein the isoflavone level is less than about 60% of the wild type plant. The isoflavone level can be less than about 55%, about 50%, about 45%, about 40%, about 35%, about 30%, about 25%, about 20%, about 15%, about 10%, about 5%, or about 0% of the wild type plant. The reduced isoflavone can be daidzin, genistin, glycitin, daidzein, genistein, or glycitein, or all of the above.

In one embodiment, the isoflavone level is reduced by reducing expression of an isoflavone synthase (IFS) gene, preferably by a non-transgenic mutation of an IFS gene, such as a stop or missense mutation, but in other embodiments, by expression of a transgene.

In some embodiments, the isoflavone level is reduced by a non-transgenic mutation of an IFS1 gene. For example, the IFS1 gene may include a mutation which results in a change of amino acid 128 of SEQ ID NO: 3, preferably where the change is from a tryptophan to a stop codon or the IFS1 gene may include a change around nucleotide 450 of SEQ ID NO: 1.

In other embodiments, the isoflavone level of the non-naturally occurring soybean plants described above is reduced by a non-transgenic mutation of an IFS2 gene. For example, the IFS2 gene may include a mutation which results in a change of amino acid 158 of SEQ ID NO: 4, in particular, wherein the change is from a lysine to an asparagine or wherein the IFS2 gene includes a change around nucleotide 525 of SEQ ID NO: 2.

In another aspect, this disclosure concerns a plant containing the mutated isoflavone synthase gene, as well as seeds, pollen, plant parts and progeny of that plant.

In yet another aspect, this disclosure concerns food and non-food products incorporating soybean seeds having reduced isoflavones.

In still yet another aspect, this disclosure concerns a soybean plant having seeds with reduced isoflavones compared to the seeds of wild type soybean plants created by: (a) obtaining plant material from a parent soybean plant; (b) inducing at least one mutation in at least one isoflavone synthase gene of the plant material by treating the plant material with a mutagen to create mutagenized plant material; (c) analyzing progeny soybean plants to detect at least one mutation in at least one isoflavone synthase gene. The plant material can be seeds, pollen, plant cells, or plant tissue. The mutagen can be ethyl methanesulfonate, preferably, at a concentration from about 0.2 to about 1.6%. In some embodiments, the method also includes the steps of analyzing the progeny soybean plants by isolating genomic DNA from the mutagenized plant material or its progeny; and amplifying segments of an isoflavone synthase gene in the isolated genomic DNA using primers specific to the isoflavone synthase gene or to the DNA sequences adjacent to the isoflavone synthase gene. In some embodiments, at least one primer has a sequence substantially homologous to SEQ ID Nos. 3 and 4.

BRIEF DESCRIPTION OF THE DRAWING FIGURES

FIG. 2 depicts an allelic series of mutations found in IFS1 and IFS2 through the use of TILLING® technology.

Figure 6:
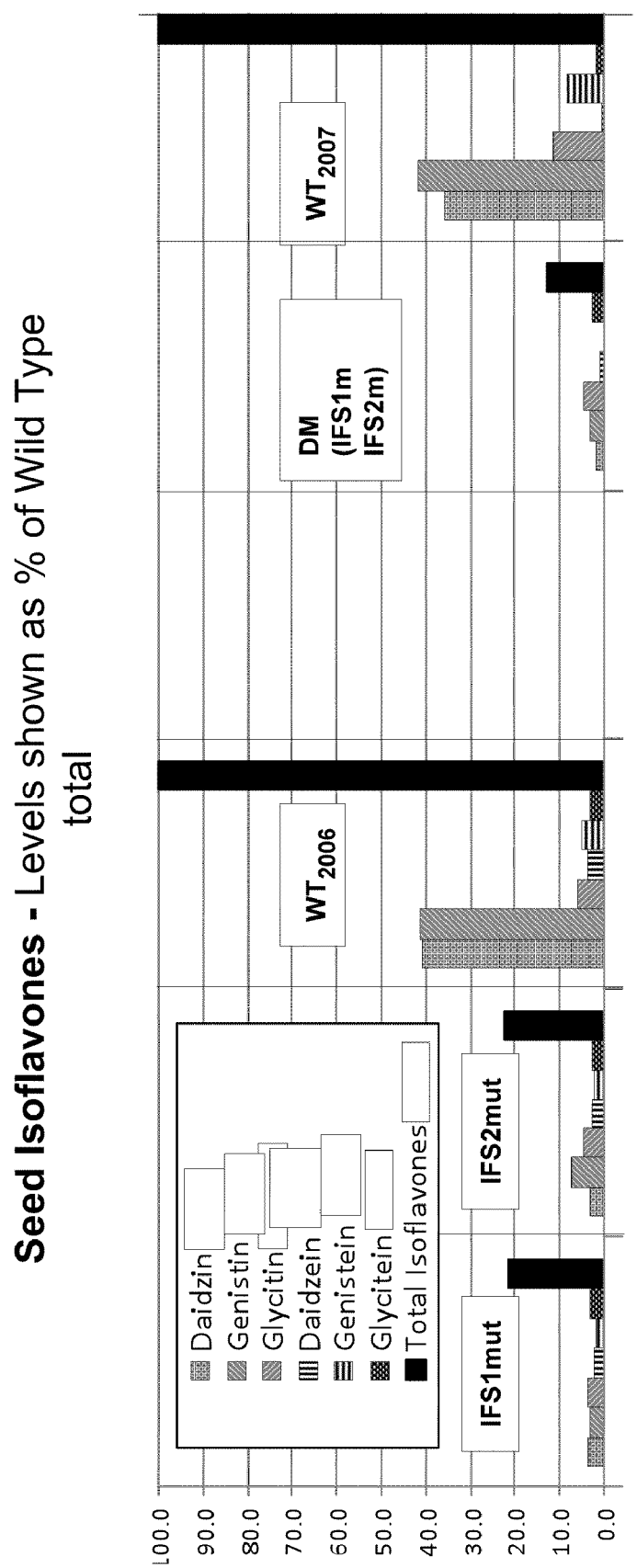

FIG. 6 depicts the levels of individual and total isoflavones in double mutant and WT seed shown as a percentage of WT from 2006 and 2007. Soybean seeds were evaluated for their levels of different isoflavones. On the left, seeds homozygous for either the IFS1 W128* mutation (IFS1mut) or the IFS2 K158N mutation (IFS2mut) are compared with unmutated seed grown at the same time (WT2006). On the right, seeds from DM plants (IFS1 W128*/IFS2 K158N/IFS2 WT) are compared with unmutated seed grown at the same time (WT2007).

BRIEF DESCRIPTION OF THE SEQUENCE LISTING

SEQ ID NO: 1 shows *glycine max* isoflavone synthase 1 mRNA, complete cds. (GenBank Accession Number AF195798).

SEQ ID NO: 2 shows *glycine max* isoflavone synthase 2 gene, complete cds. (GenBank Accession Number AF195819).

SEQ ID NO: 3 shows the protein encoded by SEQ ID NO: 1 (NCBI Accession Number AAF34519).

SEQ ID NO: 4 shows the protein encoded by SEQ ID NO: 2 (NCBI Accession Number AAF45143).

SEQ ID NOs: 5 through 12 show the DNA sequence of the specific PCR primers for isoflavone synthase 1 and isoflavone synthase 2 used to identify mutations described herein.

DETAILED DESCRIPTION OF PREFERRED EMBODIMENTS

The present disclosure describes soybean plants having seeds with reduced isoflavones. In preferred embodiments, the reduced isoflavone level is due to non-transgenic mutations and not the inclusion of foreign nucleic acids in the soybean plants' genomes. It should be understood that plants having these non-transgenic mutations may be bred with other transgenic plants having desired characteristics, i.e., herbicide resistance, or transformed with transgenes in order obtain other non-naturally occurring soybean plants with desired characteristics.

The present disclosure further describes a series of independent non-transgenic human-induced mutations in one or more isoflavone synthase genes; soybean plants having these mutations in one or more isoflavone synthase genes thereof; and a method of creating and identifying similar and/or additional mutations in one or more isoflavone synthase genes of soybean plants.

DEFINITIONS

As used herein, the term "isoflavone synthase gene" or its abbreviation "IFS gene" refers to isoflavone synthase 1 gene, isoflavone synthase gene 2, homologs, orthologs, paralogs and variants thereof. The term "isoflavone synthase 1 gene" or its abbreviation "ISF1" refers to variants, orthologs, homologs, paralogs, and functional equivalents of SEQ ID NO: 1 that code for proteins that are similar to SEQ ID NO: 3. The term isoflavone synthase 2 or its abbreviation, "ISF2") refers to variants orthologs, homologs, paralogs, and functional equivalents of SEQ ID NO: 2 that code for proteins that are similar to SEQ ID NO: 4.

As used herein, the term "non-naturally occurring" when used in reference to a soybean plant means a soybean plant that has been genetically modified by man, for example, by expression of a transgene or induction of a mutation in a gene or regulatory element of the gene by calculated exposure to a mutagenic agent, such as a chemical mutagen, or an "insertional mutagen," such as a transposon. Furthermore, a plant generated by cross breeding different strains and varieties is also considered a "non-naturally occurring plant" because the selection and breeding is performed by human intervention. In contrast, a soybean plant containing only spontaneous or naturally occurring mutations is not a "non-naturally occurring soybean plant" as defined herein and, therefore, is described herein. One skilled in the art understands that while a non-naturally occurring soybean plant typically has a nucleotide sequence that is altered as compared to a similar naturally occurring soybean plant, a non-naturally occurring soybean plant also can be genetically modified by human intervention without altering its nucleotide sequence, for example, by modifying its methylation pattern.

Overview

The described non-naturally occurring soybean plants and seeds can have isoflavone levels that are reduced by any amount as compared to wild type soybean plants and seeds, such as, for example, less than about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or about 0% of wild type levels. The described non-naturally occurring soybean plants may have an equivalent reduction in all isoflavones naturally found in soybean plants (i.e., a reduction in total isoflavone level) or varying levels of reduction of the isoflavones naturally found in soybean plants, such as daidzin, genistin, glycitin, daidzein, genistein, and glycitein.

Reduction of Isoflavone Levels

These non-naturally occurring soybean plants and seeds having reduced isoflavone levels can be created using any methods known to those of skill in the art, including inhibiting the expression of an IFS gene and/or reducing the stability of the IFS protein. In preferred embodiments, the expression of multiple IFS genes, for example, IFS1 and IFS2, or IFS1, IFS2-1, and IFS2-2, is modulated, but in some embodiments, only the expression of a single IFS gene or protein is modulated.

Antisense

In some embodiments, antisense technology is used to prevent the translation of target mRNA, such as IFS mRNA. As such, antisense technology generally reduces the levels of the target protein, here IFS protein. An IFS gene or fragments thereof can be introduced into the plant in antisense orientation. The fragments can be as small as 18 nucleotides and as large as 3,000 nucleotides or larger. cDNA fragments of an IFS gene can be cloned into a vector (for example, pCAMBIA1302) in the opposite orientation as the native gene. The inverted transcript will form a heteroduplex structure with the native IFS gene transcript, which is then degraded before translation. The sense and antisense sequences need not be identical, even partial homology can be sufficient to achieve suppression of target gene expression. So, a sequence of IFS from one soybean cultivar can be used to suppress IFS gene expression in another cultivar, without knowing the sequence of the IFS gene orthologs from that cultivar.

RNA Interference

In other embodiments, RNA interference (RNAi) is used to eliminate target mRNA. There are variations in the construction of vectors for RNAi, but the basic result is the formation of a hairpin loop structure in the RNA (Horiguchi 2004). A fragment of an IFS nucleotide sequence in the opposite direction to its cDNA can be cloned into a vector to result in an inverted hairpin structure in the mRNA. These hairpin structures are cleaved into small fragments by an endonuclease named Dicer, whose function is to prevent erroneous transcripts from being translated (Hamilton and Baulcombe, Science 286(5441): 950-952, 1999; Matzke et al., Science 293 (5532): 1080-1083, 2001). The small fragments of mRNA are generally about 20 to 21 nucleotides in size, and have been termed siRNAs, or small interfering RNAs. Larger and smaller fragments can also be utilized. These siRNAs can downregulate the expression of homologous genes. Again, the homology need not be complete, so sequences detailed here could be used to create RNAi constructs for other soybean species.

Mutagenesis

In some embodiments, isoflavone levels are reduced by non-transgenic means, such as creating a mutation of an IFS gene. Chemical mutagens such as EMS (methanesulfonic acid, ethyl ester) and both gamma ray and fast neutron radiation can create mutations in DNA. Some examples of mutations are deletions, insertions, and missense mutations. After mutation, screening can be done to identify deletions that create premature stop codons or otherwise non-functional IFS genes. Screening of mutants can be done by sequencing, or by the use of probes or primers specific to the IFS genes or protein. Specific mutations in IFS genes can also be created by TILLING® (Targeted Induced Local Lesion of Genome), which is described in greater detail below, and tDNA insertion. Such mutations can result in decreases in IFS gene expression, decreased stability of IFS mRNA, or decreased stability of the IFS protein. Such plants as defined herein are non-naturally occurring.

The described soybean plants can have any combination of mutations which results in reduced isoflavone levels. For example, the described soybean plants may have a single mutation in a single IFS gene, multiple mutations in a single IFS gene, or mutations in both the IFS1 and IFS2 genes.

TILLING®

In preferred embodiments, a method known as TILLING® is utilized to create and identify the isoflavone synthase mutations and soybean plants. See McCallum et al., Nature Biotechnology (April 2000), 18: 455-457; McCallum et al., Plant Physiology 123: 439-442, 2000; and U.S. Pat. Nos. 5,994,075 and 20040053236, all of which are incorporated herein by reference. In the basic TILLING® methodology, plant material, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

Any cultivar of soybean having at least one isoflavone synthase gene with substantial homology to SEQ ID NO: 1 or 2 may be used. The homology between the isoflavone synthase gene and SEQ ID NO: 1 or 2 may be as low as 60% provided that the homology in the conserved regions of the gene is higher. One of skill in the art may prefer a soybean cultivar having commercial popularity or one having specific desired characteristics in which to create the isoflavone synthase-mutated soybean plants. Alternatively, one of skill in the art may prefer a soybean cultivar having few polymorphisms, such as an in-bred cultivar, in order to facilitate screening for mutations within an isoflavone synthase locus.

In one embodiment, seeds from soybean plants are mutagenized and then grown into M1 plants. The M1 plants were then allowed to self-pollinate and seeds from the M1 plant are grown into M2 plants, which are then screened for mutations in their isoflavone synthase loci. Though the mutagenized plant material can be screened for mutations, an advantage of screening the M2 plants is that all somatic mutations correspond to germline mutations. One of skill in the art would understand that a variety of soybean plant materials, including but not limited to, seeds, pollen, plant tissue or plant cells, may be mutagenized in order to create the isoflavone synthase-mutated soybean plants. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen; thus these M1 plants may then be screened for isoflavone synthase mutations instead of waiting until the M2 generation.

Mutagens that create primarily point mutations and short deletions, insertions, transversions, and or transitions (about 1 to about 5 nucleotides), such as chemical mutagens or radiation, may be used to create the mutations. Mutagens conforming with the methods described herein include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino]acridine dihydrochloride (ICR-170), and formaldehyde. Spontaneous mutations in an isoflavone synthase locus that may not have been directly caused by the mutagen can also be identified using the disclosed methods.

Any method of plant DNA preparation known to those of skill in the art may be used to prepare the soybean plant DNA for isoflavone synthase mutation screening. For example, see Chen & Ronald, Plant Molecular Biology Reporter 17:53-57, 1999; Stewart & Via, Bio Techniques 14:748-749, 1993. Additionally, several commercial kits are available, including kits from Qiagen® (Valencia, Calif.) and Qbiogene (Carlsbad, Calif.).

Prepared DNA from individual soybean plants can pooled in order to expedite screening for mutations in an isoflavone synthase gene of the entire population of plants originating from the mutagenized plant tissue. The size of the pooled group is dependent upon the sensitivity of the screening method used. Preferably, groups of four or more individuals are pooled.

After the DNA samples are pooled, the pools can be subjected to isoflavone synthase sequence-specific amplification techniques, such as Polymerase Chain Reaction (PCR). For a general overview of PCR, see PCR Protocols: A Guide to Methods and Applications (Inns, M., Gelfand, D., Sninsky, J., and White, T., eds.), Academic Press, San Diego, 1990). Any primer specific to an isoflavone synthase gene or the sequences immediately adjacent to an isoflavone synthase gene may be utilized to amplify the isoflavone synthase sequences within the pooled DNA sample. Preferably, the primer is designed to amplify the regions of an isoflavone synthase locus where useful mutations are most likely to arise. Most preferably, the primer is designed to detect mutations within exonic regions of the isoflavone synthase. Additionally, it is preferable for the primer to avoid known polymorphic sites in order to ease screening for point mutations. To facilitate detection of PCR products on a gel, the PCR primer may be labeled using any conventional labeling method.

Primers can be designed based upon the isoflavone synthase sequences, isoflavone synthase 1 (GenBank accession number AF195798; SEQ ID NO: 1) and isoflavone synthase 2 (GenBank accession number AF195819; SEQ ID NO: 2).

The proteins encoded by this sequence are shown in SEQ ID NOs: 3 and 4, respectively. Exemplary primers (SEQ ID NOs: 5-12) that have proven useful in identifying useful mutations within the isoflavone synthase sequences are shown below in Table 1.

TABLE 1

Exemplary PCR Primers

| SEQ ID NO | Primer Name | Primer ID | Primer Sequence |
|---|---|---|---|
| 5 | GmIFS 1-A2F | 2167 | CTCGGGATCACAGAAACCAACAACAGTTC |
| 6 | GmIFS 1-A1R | 2189 | GTCCATTTGAGAAGCTCCTCGGTGACG |
| 7 | GmIFS 2-AF | 2174 | CCTCACAAAAGCAAAGATCAAACAAACCAA |
| 8 | GmIFS 2-AR | 2175 | CATTTCAGAAGCTCCTCGGTCAAGTCAAG |
| 9 | GmIFS 2-BF | 2176 | CTTCCCAACGCCACCACTGTAAACAAG |
| 10 | GmIFS 2-BR | 2177 | CGTACCGTTAATTAATTGCCACCACATGAA |
| 11 | GmIFS 2-CF | 2178 | ATGGAGATCAAAATCACCAAGGACCACATC |
| 12 | GmIFS 2-CR | 2179 | TGTCTCTAGGAACCTCTCAGGACGGAACTC |

The PCR amplification products may be screened for isoflavone synthase mutations using any method that identifies nucleotide differences between wild type and mutant sequences. These may include, for example but not limited to, sequencing, denaturing high pressure liquid chromatography (dHPLC), constant denaturant capillary electrophoresis (CDCE), temperature gradient capillary electrophoresis (TGCE) (Li et al., Electrophoresis 23(10):1499-1511, 2002) or by fragmentation using enzymatic cleavage, such as used in the high throughput method described by Colbert et al., Plant Physiology 126:480-484, 2001. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program.

Mutations that reduce isoflavone synthase function are desirable. Preferred mutations include missense, nonsense and splice junction mutations, including mutations that prematurely truncate the translation of an isoflavone synthase protein from messenger RNA, such as those mutations that create a stop codon within the coding region of the gene. These mutations include insertions, repeat sequences, modified open reading frames (ORFs) and, most preferably, point mutations. Each mutation is evaluated in order to predict its impact on protein function (i.e., completely tolerated to loss-of-function) using bioinformatics tools such as SIFT (Sorting Intolerant from Tolerant; Ng, P. C. and Henikoff, S. SIFT: predicting amino acid changes that affect protein function. Nuc Acids Res 31:3812-3814, 2003), PSSM (Position-Specific Scoring Matrix; Henikoff, J. G. and Henikoff, S. Using substitution probabilities to improve position-specific scoring matrice. Comput Appl Bios 12:135-143, 1996) and PARSESNP (Taylor N. E. and Greene, E. A. PARSESNP: A tool for the analysis of nucleotide polymorphisms. Nuc Acids Res 31:3808-3811, 2003). For example, a SIFT score that is less than 0.05 and a large change in PSSM score (roughly 10 or above) indicate a mutation that is likely to have a deleterious effect on protein function.

Once an M2 plant having a mutated isoflavone synthase sequence is identified, the mutations are analyzed to determine its affect on the expression, translation, and/or level of the isoflavone synthase protein. First, the PCR fragment containing the mutation is sequenced, using standard sequencing techniques, in order to determine the exact location of the mutation in relation to the overall isoflavone synthase sequence.

If the initial assessment of the mutation in the M2 plant appears to be of a useful nature and in a useful position within the isoflavone synthase gene, then further phenotypic analysis of the soybean plant containing that mutation is pursued. First, the M2 plant is outcrossed twice in order to eliminate background mutations. Then the outcrossed plant is self-pollinated in order to create a plant that is homozygous for the isoflavone synthase mutation. However, if a isoflavone synthase mutation results in complete male sterility, the M2 plant can not be self-pollinated in order to create a homozygous line. The male sterile phenotype may be carried in a heterozygous state by crossing with pollinator lines having the wild type gene.

Biochemical characteristics of these homozygous isoflavone synthase mutant plants are assessed to determine if the mutation results in a useful phenotypic change in the soybean. Mutations in multiple isoflavone synthase genes can be combined by standard breeding to lead to a greater phenotypic change.

Exemplary mutations are provided below. It is to be understood that the mutations below are merely exemplary and that similar mutations are also contemplated. For example, in addition to W128* and G450A, row 1 of Table 2 also describes other similar mutations with similar phenotypic effect, such as any mutation which results in a change in amino acid 128 of SEQ ID NO: 3 and any mutation around nucleotide 450 of SEQ ID NO: 1.

The following mutations shown in Table 2 are exemplary of the mutations created and identified in isoflavone synthase 1. Nucleotide mutations and amino acid mutations are numbered according to SEQ ID NOs: 1 and 3, respectively.

TABLE 2

Mutations in Isoflavone Synthase 1

| Primer Set | Nucleotide Mutation | Amino Acid Mutation | PSSM Score | SIFT Score | Score |
|---|---|---|---|---|---|
| 2167, 2189 | G450A | W128* | Stop | Stop | Stop |
| 2167, 2189 | G176A | S37N | | 0.07 | Severe Missense |
| 2167, 2189 | C190T | L42F | 6.6 | 0.06 | Severe Missense |
| 2167, 2189 | C208T | L48F | 12 | 0.01 | Severe Missense |
| 2167, 2189 | C211T | H49Y | 22.9 | 0.00 | Severe Missense |
| 2167, 2189 | C242T | A59V | 12.3 | 0.10 | Severe Missense |
| 2167, 2189 | C403T | L113F | 13 | 0.01 | Severe Missense |
| 2167, 2189 | A464T | K133M | 19.7 | 0.00 | Severe Missense |
| 2167, 2189 | C466T | L134F | 12 | 0.01 | Severe Missense |
| 2167, 2189 | G600C | E178D | 15.4 | 0.02 | Severe Missense |
| 2167, 2189 | G478A | D138N | 14.3 | 0.01 | Severe Missense |
| 2167, 2189 | C497T | T144I | 11.6 | 0.02 | Severe Missense |
| 2167, 2189 | T436C | F124L | 15.2 | 0.02 | Severe Missense |
| 2167, 2189 | C281T | S72F | 12.3 | 0.29 | Missense |
| 2167, 2189 | C302T | P79L | 12.4 | 0.13 | Missense |
| 2167, 2189 | C314T | A83V | 6.2 | 0.17 | Missense |
| 2167, 2189 | G134A | S23N | | 0.33 | Missense |
| 2167, 2189 | C232T | L56F | | 0.13 | Missense |
| 2167, 2189 | C287T | S74F | −4.5 | 0.69 | Missense |
| 2167, 2189 | G176A | S37N | | 0.07 | Missense |
| 2167, 2189 | T455A | F130Y | 9.8 | 0.08 | Missense |

The following mutations shown in Table 3 are exemplary of the mutations created and identified in isoflavone synthase 2.

Nucleotide mutations and amino acid mutations are numbered according to SEQ ID NOs: 2 and 4, respectively.

TABLE 3

Mutations in Isoflavone Synthase 2

| Primer Set | Nucleotide Mutation | Amino Acid Mutation | PSSM Score | SIFT Score | Score |
|---|---|---|---|---|---|
| 2176, 2177 | A823T | R258* | Stop | Stop | Stop |
| 2178, 2179 | G1132A | W315* | Stop | Stop | Stop |
| 2174, 2175 | A244D | Frameshift | | | Stop |
| 2174, 2175 | C139T | R30C | | 0 | Severe Missense |
| 2174, 2175 | A341T | E97V | 24.7 | 0 | Severe Missense |
| 2174, 2175 | C427T | P126S | 19.5 | 0.02 | Severe Missense |
| 2174, 2175 | G463A | D138N | 13.7 | 0.01 | Severe Missense |
| 2174, 2175 | G525T | K158N | 12.8 | 0.01 | Severe Missense |
| 2176, 2177 | T539C | M163T | 19.2 | 0.01 | Severe Missense |
| 2176, 2177 | G938A | G296D | 17.4 | 0.01 | Severe Missense |
| 2176, 2177 | G637A | E196K | 15.6 | 0.02 | Severe Missense |
| 2176, 2177 | G640A | E197K | 12.7 | 0.05 | Severe Missense |
| 2176, 2177 | G661A | E204K | 14.2 | 0.02 | Severe Missense |
| 2176, 2177 | C691T | L214F | 10.9 | 0.01 | Severe Missense |
| 2176, 2177 | A725T | K225M | 16.4 | 0.01 | Severe Missense |
| 2176, 2177 | A757T | I236F | 15.6 | 0.01 | Severe Missense |
| 2176, 2177 | C776T | P242L | 15.6 | 0.05 | Severe Missense |
| 2176, 2177 | G806A | R252H | | 0.02 | Severe Missense |
| 2176, 2177 | A856T | S269C | 8.9 | 0.2 | Severe Missense |
| 2178, 2179 | G1106A | D307N | 20.4 | 0.00 | Severe Missense |
| 2178, 2179 | G1115A | A310T | 21.3 | 0.00 | Severe Missense |
| 2178, 2179 | G1118A | V311M | 12.6 | 0.01 | Severe Missense |
| 2178, 2179 | G1139A | A318T | 15.2 | 0.01 | Severe Missense |
| 2178, 2179 | C1145T | L320F | 15.6 | 0.01 | Severe Missense |
| 2178, 2179 | C1157T | P324S | 13.0 | 0.03 | Severe Missense |
| 2178, 2179 | G1184A | E333K | | 0.00 | Severe Missense |
| 2178, 2179 | C1214T | L343F | 13.1 | 0.01 | Severe Missense |
| 2178, 2179 | C1244T | P353S | 24.8 | 0.00 | Severe Missense |
| 2178, 2179 | C1286T | P367S | 24.8 | 0.00 | Severe Missense |
| 2178, 2179 | A1374T | N396I | 27.1 | 0.00 | Severe Missense |
| 2174, 2175 | C148T | P33S | | 0.19 | Missense |
| 2174, 2175 | C155T | P35L | | 0.24 | Missense |
| 2174, 2175 | A245T | K65I | 13.2 | 0.06 | Missense |
| 2174, 2175 | C479T | T143I | 13.7 | 0.08 | Missense |
| 2174, 2175 | G208T | D53Y | | 0.07 | Missense |
| 2174, 2175 | C385T | R112C | 12.9 | 0.18 | Missense |
| 2176, 2177 | C565T | P172S | 4.2 | 0.6 | Missense |
| 2176, 2177 | G682A | E211K | 5.6 | 0.15 | Missense |
| 2176, 2177 | G739A | E230K | 1.2 | 0.58 | Missense |
| 2176, 2177 | G746A | R232K | 8.4 | 0.1 | Missense |
| 2176, 2177 | G838A | V263I | | 0.97 | Missense |
| 2176, 2177 | G850A | E267K | | 0.22 | Missense |
| 2176, 2177 | G860A | G270E | 11.8 | 0.21 | Missense |
| 2178, 2179 | G1133A | A316T | 7.2 | 0.16 | Missense |
| 2178, 2179 | G1187A | V334I | | 1.00 | Missense |
| 2178, 2179 | G1298A | V371M | −3.3 | 0.81 | Missense |
| 2178, 2179 | G1301A | V372I | 7.5 | 0.12 | Missense |
| 2178, 2179 | G1358A | A391T | 0.2 | 0.97 | Missense |

Testing of Isoflavone Levels

Isoflavone levels of plants and seeds can be analyzed using any standard method known to those of skill in the art, such as the methods outlined in Thomas et al. (J Chromatogr B Biomed Sci Appl 760:191-205, 2001) and Kirakosyan et al. (J. Agri. Food Chem 54:54-58, 2006).

The following Examples are offered by way of illustration, not limitation.

EXAMPLE 1

Mutagenesis

In one embodiment, soybean seeds were placed on a shaker (45 rpm) in a fume hood at ambient temperature. The mutagen ethyl methanesulfonate (EMS) was added to the imbibing seeds to final concentrations ranging from about 0.2% to about 1.6% (v/v). Following an incubation of 6 to 24 hours, the EMS solution was replaced 4 times with fresh H$_2$O. The seeds were then rinsed under running water for approximately 1 hour. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from these M2 plants was extracted and prepared in order to identify which M2 plants carried a mutation at their isoflavone synthase loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next 400 µl of solution AP1 [Buffer AP1, solution DX and RNase (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5600×g. Next, 800 µl of Buffer AW was added to each well of the filter plate, sealed and spun for 15 minutes at 5600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

TILLING®

The M2 DNA was pooled into groups of six individual plants. The DNA concentration for each individual within the pool was approximately 0.033 ng/µl with a final concentration of 0.2 ng/µl for the entire pool. Then, 5 µl of the pooled DNA samples 1 ng was arrayed on microtiter plates and subjected to gene-specific PCR.

PCR amplification was performed in 15 µl volumes containing 2.5 ng pooled DNA, 0.75×ExTaq buffer (Panvera®, Madison, Wis.), 2.6 mM $MgCl_2$, 0.3 mM dNTPs, 0.3 µM primers, and 0.05 U Ex-Taq (Panvera®) DNA polymerase. PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63-61° C. for 30 seconds, ramp 0.5° C./sec to 72° C., 72° C. for 1 minute; 72° C. for 8 minutes; 98° C. for 8 minutes; 80° C. for 20 seconds; 60 cycles of 80° C. for 7 seconds −0.3 degrees/cycle.

The PCR primers (MWG Biotech, Inc., High Point, N.C.) were mixed as follows: 2.5 µl 100 µM IRD-700 labeled left primer; 7.5 µl 100 µM left primer; 9.0 µl 100 µM IRD-800 labeled right primer; and 1.0 µl 100 µM right primer.

A label can be attached to each primer as described or to only one of the primers. Alternatively, Cy5.5 modified primers could be used. The label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, and CEL 1 (Transgenomic®, Inc.; 1:100,000 dilution) was added with mixing on ice, and the plate was incubated at 45° C. for 15 min. The specific activity of the CEL1 was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at 80° C., spun at 4,000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 h at 1,500-V, 40-W, and 40-mA limits at 50° C.

During electrophoresis, the gel was imaged using a LI-COR® (Lincoln, Nebr.) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING® individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation).

Isoflavone Content

Soy seeds (2 g) and a commercial soy flour control (purchased at a retail co-op) were ground in liquid nitrogen using a mortar and pestle, sent to BioProfile Testing Laboratories, LLC (Minneapolis, Minn.) where the samples were extracted and analyzed blindly for isoflavone content according to the methods outlined in Thomas et al. (J Chromatogr B Biomed Sci Appl 760:191-205, 2001) and Kirakosyan et al. (J. Agri. Food Chem 54:54-58, 2006).

Isoflavone levels of wild type (WT) control seeds, soy flour and seeds from soybean plants carrying mutations in IFS1 or IFS2 are shown in Table 4. Serial dilution of wild type samples WT834 shows the linearity of the assay measurements.

TABLE 4

| | Isoflavone Content (µg/kg) | | | | | | |
|---|---|---|---|---|---|---|---|
| | Daidzin | Glycitin | Genistin | Daizein | Glycitein | Genistein | Total |
| Soy flour from co-op | 678.6 | 152.3 | 645.3 | 49.4 | 209.6 | 106.2 | 1841.5 |
| WT834 | 623.4 | 91 | 631.9 | 52.8 | 52 | 78.3 | 1529.4 |
| IFS1-W128* | 68.9 | 68.6 | 61.7 | 43.4 | 57 | 30.3 | 329.9 |
| IFS2-K158N | 45.7 | 71.4 | 109.6 | 40.9 | 44.8 | 34.2 | 346.5 |
| IFS2-W315* | 69.8 | 94.5 | 173.9 | 18.8 | 119.9 | 29.5 | 506.4 |
| WT834 (100 mg) | 527.9 | 142.6 | 584.5 | 49.9 | 42.4 | 86.2 | 1433.5 |
| WT834 (50 mg) | 468.6 | 108.3 | 535.7 | 44.3 | 45.4 | 75.8 | 1278.1 |

Identification and Evaluation of IFS1-Mutation W128*

DNA from a soybean plant originating from seeds that were incubated in EMS was amplified using primers 2167 and 2189 (SEQ ID NOs: 5 and 6). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in the isoflavone synthase sequence. Sequence analysis of this fragment showed the mutation was a G to A change at nucleotide 450 of SEQ ID NO: 1. This mutation was associated with a change from tryptophan (W) to a stop codon at amino acid 128 of the isoflavone synthase 1 protein shown in SEQ ID NO: 3.

Total isoflavone levels in seeds from soybean plants carrying the W128* mutation in IFS1 were reduced to approximately 21% of wild type levels. The greatest percent reductions were seen in daidzin (approximately 11% of wild type) and genistin (approximately 19.7% of wild type).

Identification and Evaluation of IFS2-Mutation K158N

DNA from a soybean plant originating from seeds that were incubated in EMS was amplified using primers 2174 and 2175 (SEQ ID NOs: 7 and 8). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in the isoflavone synthase sequence. Sequence analysis of this fragment showed the mutation was a G to T change at nucleotide 525 of SEQ ID NO: 2. This mutation was associated with a change from lysine (K) to asparagine (N) at amino acid 158 of the isoflavone synthase 2 protein shown in SEQ ID NO: 4.

Total isoflavone levels in seeds from soybean plants carrying the K158N mutation in IFS2 were reduced to approximately 23% of wild type levels. The greatest percent reductions were seen in daidzin (approximately 7.3% of wild type) and genistin (approximately 17.3% of wild type).

Identification and Evaluation of IFS2-Mutation W315*

DNA from a soybean plant originating from seeds that were incubated in EMS was amplified using primers 2178 and 2179 (SEQ ID NOs: 11 and 12). The PCR amplification products were then incubated with CEL 1 and electrophoresed. The electrophoresis gel image showed a fragment that stood out above the background pattern for the PCR amplification products. Therefore, it was likely that this fragment contained a heteroduplex created by a mutation in the isoflavone synthase sequence. Sequence analysis of this fragment showed the mutation was a G to A change at nucleotide 1132 of SEQ ID NO: 2. This mutation was associated with a change from tryptophan (W) to a stop codon at amino acid 315 of the isoflavone synthase 2 protein shown in SEQ ID NO: 4.

Total isoflavone levels in seeds from soybean plants carrying the W315* mutation in IFS2 were reduced to approximately 33% of wild type levels. The greatest percent reductions were seen in daidzin (approximately 11% of wild type) and genistin (approximately 27.5% of wild type).

EXAMPLE 2

Figure 1:
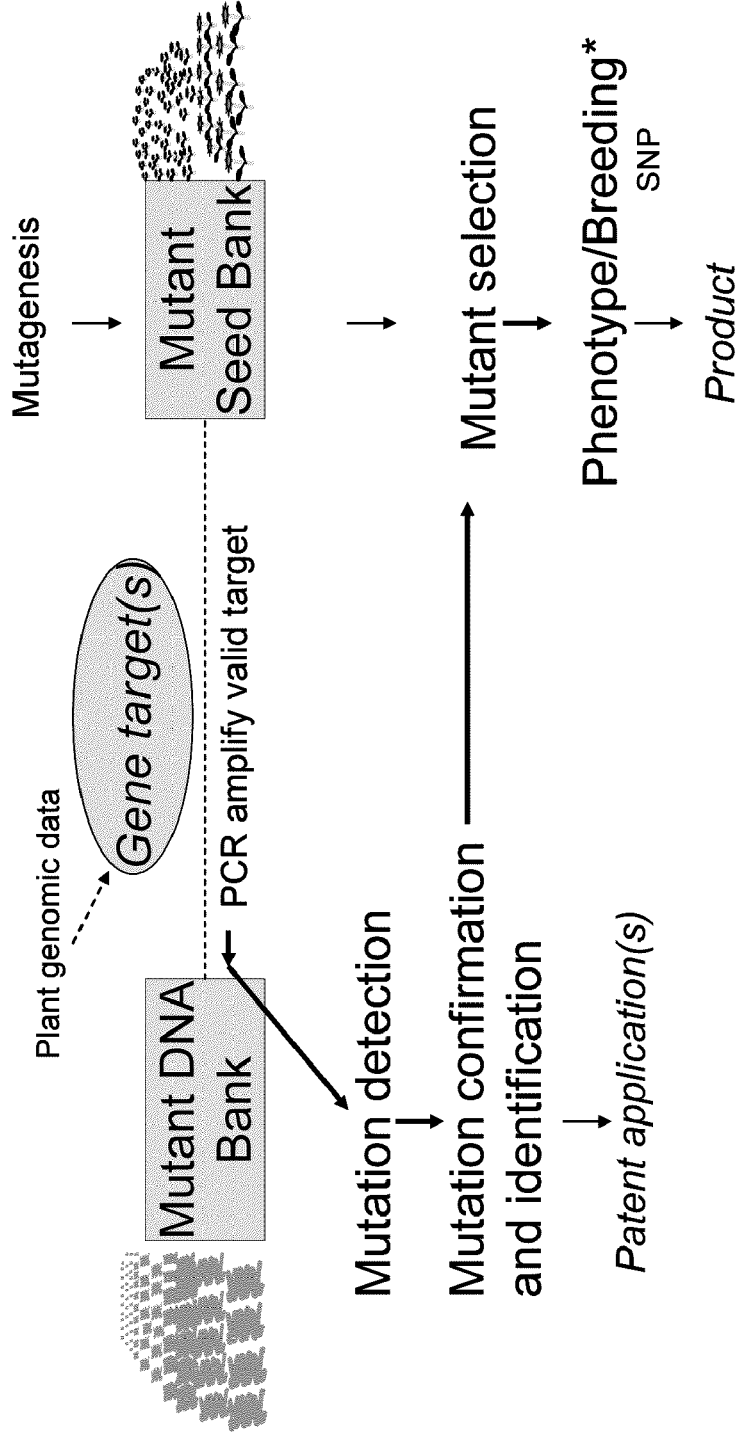
FIG. 1 depicts the TILLING® process.

Use of TILLING® to Identify Double Mutant Soybean Plants with Reduced Isoflavone Levels TILLING® was used to select plants carrying IFS1 and IFS2 nonsense and missense mutations that once combined result in an approximately 90% reduction in isoflavones (See FIG. 1 for an overview of the process). Here we show that there must be at least two loci of the IFS2 gene present in the genome and that they behave in an additive manner. We present genotypic and phenotype data for plants carrying a mutation in one of these genes and evaluate the contribution of the IFS1 gene and each IFS2 gene to the levels of isoflavones.

Methods

Plants containing severe missense or non-sense (stop) mutations in either IFS1 or IFS2 were selected from a soybean TILLING® library. Selected plants were selfed (if necessary) to create homozygous lines for the mutation in question. Plants were then grown in the greenhouse and sampled for seed tissue.

Soy seeds (2 g) were ground in liquid nitrogen (mortar and pestle) into a fine powder and sent to BioProfile Testing Laboratories. The samples were extracted and evaluated twice according to the methods outlined in Thomas et al. (Chromatogr B, 760:191-205, 2001) and Kirakosyan et al. (J. Agri. Food Chem. 54:54-58, 2006) using standards for each isoflavone measured.

Evidence for Two IFS2 Loci in Soybean

FIG. 2 shows an allelic series of mutations found in IFS1 and IFS2 through the use of TILLING® technology. The IFS1 mutants had the expected proportion of heterozygous and homozygous individuals for an M2 generation TILLING® population. However, evaluation of the sequencing traces of all the IFS2 mutants revealed that there were always two nucleotide peaks at the location of each of the mutations, one peak for the mutated nucleotide and one peak for the WT nucleotide at each position. Normally, two peaks indicate that the individual being sequenced is heterozygous. However, because every single mutation identified displayed two peaks, the most likely explanation for this result was that two identical genes were being amplified with the primers used. In addition, the number of mutations found by TILLING® IFS2 was about twice the number found for IFS1, further supporting the hypothesis that two IFS2 genes were present in the soybean genome.

Figure 3:
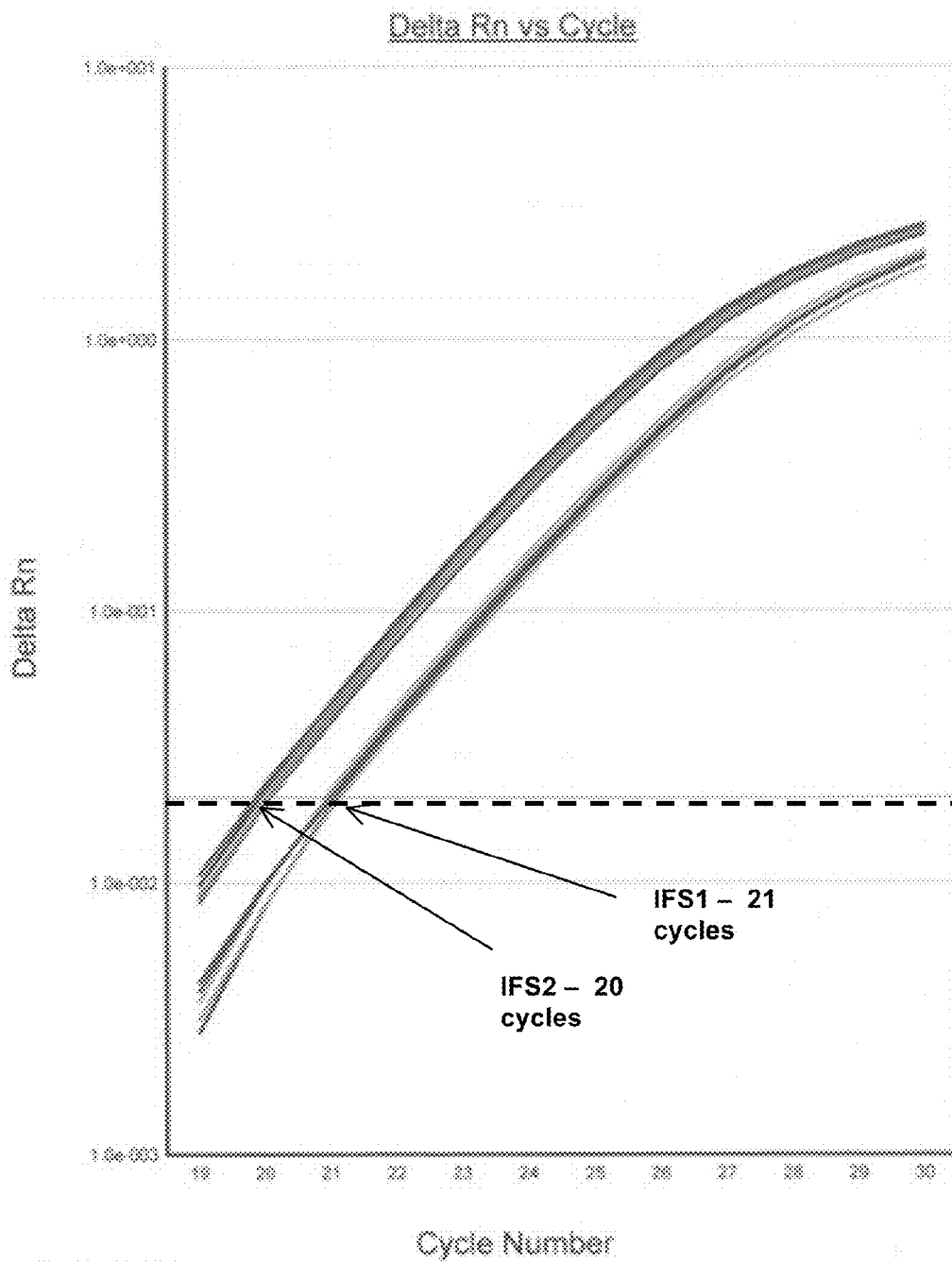
FIG. 3 depicts the sequencing results for two heterozygous IFS2 segregants showing the presence of two loci.

In order to obtain double mutant plants, IFS1 W128* and IFS2 K158N plants were crossed to each other. F1 plants containing mutations in both genes were allowed to self fertilize to produce the F2 generation. To obtain F2 plants with mutations in both IFS1 and IFS2, the plants were first genotyped to identify individuals that were homozygous for the IFS1 mutation W128*, and then the homozygous IFS1 W128* mutant plants were sequenced to determine their genotype at the two IFS2 loci. Sequence traces of the IFS2 mutants presented double peaks at the expected position for the K158N mutation. As shown in FIG. 3, some of the individuals with the K158N mutation had double peaks of equal height (top) and others have double peaks where the mutant peak was only half as high as the WT peak (bottom). If two identical genes are being PCR amplified and one gene is homozygous for a mutation whereas the other gene is homozygous WT, a sequencing trace of this individual will result in a double peak at the mutant position of equal height for each of the mutant and WT nucleotides. This is because there are equal numbers of DNA strands in the individual for both the mutant and WT sequences. However, if the individual is heterozygous for the mutation and both genes are amplified and sequenced, the mutant strand will contribute less to the sequencing reaction and as a result, the mutant peak will be less than the WT peak at that nucleotide position. Using these criteria, it was determined that there were 22 out of 384 plants with double peaks of equal size (FIG. 3). This number is consistent with the expected segregation ratio of 1/16 for the combination of IFS1m+IFS2m homozygotes, and further supports the presence of two IFS2 genes.

Figure 4:
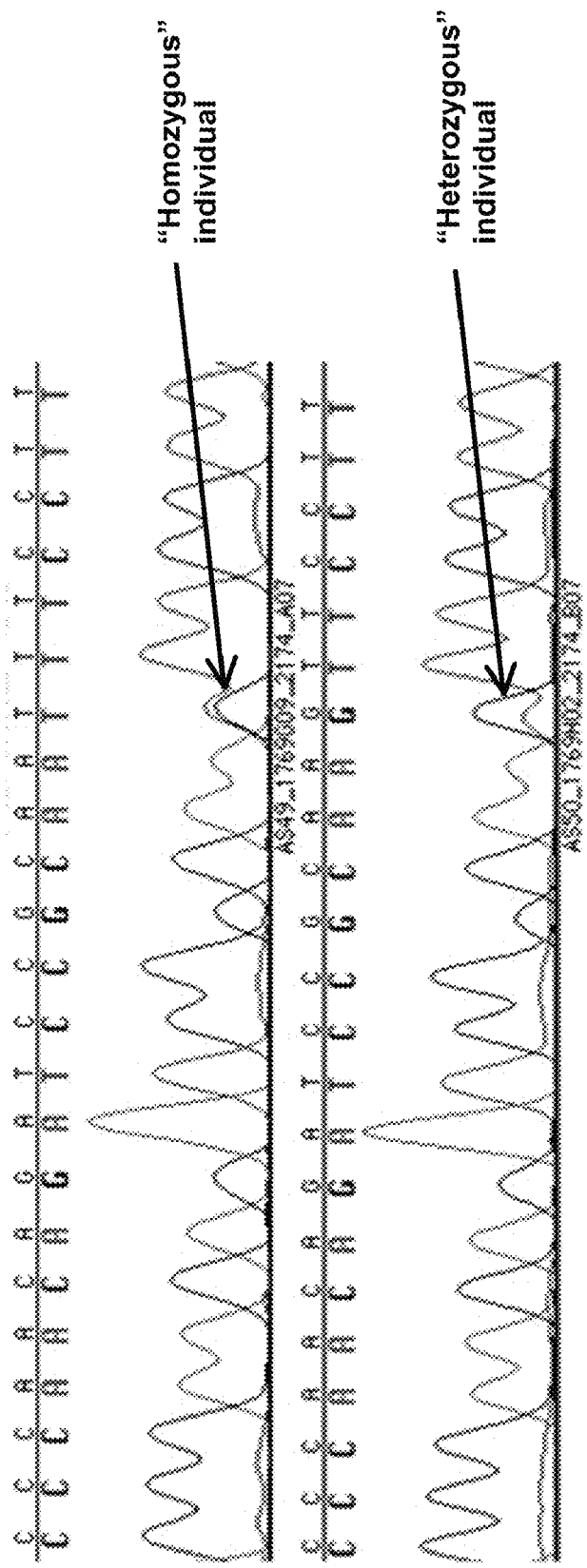
FIG. 4 depicts quantitative PCR results showing different copy number for IFS1 and IFS2.

Furthermore, it was determined that the ratio of IFS2 to IFS1 genes based on quantitative PCR is 2:1 (FIG. 4). This result is consistent with the interpretation that there are two IFS2 genes, designated herein as IFS2-1 and IFS2-2

Figure 5:
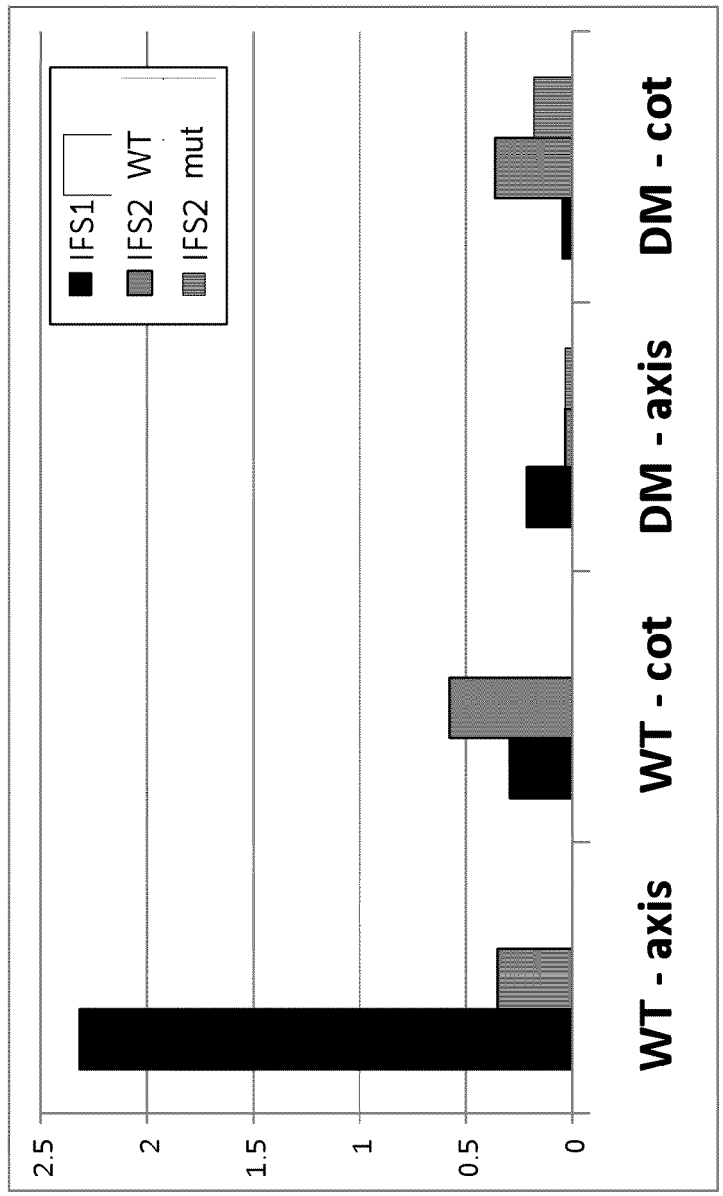
FIG. 5 depicts the RNA expression levels of IFS genes as determined with RT PCR. The expression levels of the IFS1 gene and the two IFS2 genes in the seed axis and cotyledons of wild type (WT) and double mutant (DM) plants (IFS1 mut (W128*)/IFS2 mut (K158N)/IFS2 WT) are shown relative to the expression of a control gene (IPP).

Sequence analysis of all the mutations identified by TILL-ING® indicated that there were double peaks at every mutant position, but that there were no other nucleotide positions that differed between IFS2-1 and IFS2-2. This result indicated that IFS2-1 and IFS2-2 have identical sequences except at the locations of the mutations. We have arbitrarily attributed the K158N mutation to the IFS2-1 gene. This mutation allowed us to design primers specific for the mutated gene only. Using these primers, it was determined that both IFS2-1 (K158N containing gene) and IFS2-2 genes are expressed (FIG. 5). In FIG. 5, the middle bar in each group depicts the RNA expression levels of the unmutated IFS2-2 gene (or representing both IFS2 genes in the WT plants), and the bar on the right in each group depicts the RNA expression levels of the mutated IFS2-1 gene carrying the K158N mutation. The RNA expression levels of the two IFS2 genes in the wild type (WT) tissues is represented as a single bar (the middle bar). In WT plants, the two genes have identical sequences and cannot be distinguished from each other. In contrast, the two genes can be distinguished from each other in mutant plants using primers specific for the mutated gene and for the WT gene. The RNA expression levels of the two IFS2 genes are decreased in the double mutant (DM) axis tissue (compare the middle bar in the WT axis with the contributions of the bars in the middle and on the right in the DM axis). Expression levels of the two IFS2 genes in the DM cotyledons (sum of the middle bar and the bar on the right) are about the same level as the total IFS2 expression levels in the WT cotyledons. However, the RNA expression levels of the WT IFS2-2 gene are higher than the levels of the IFS2-1 gene carrying the K158N mutation in the DM.

Since the IFS2-1 has the same sequence as IFS2-2 the mutant allelic series shown in FIG. 2 and Table 3 includes mutations in both IFS2 genes. It is not known whether IFS2-1 and IFS2-2 are linked.

Phenotype of a Double Mutant

FIG. 6 shows the levels of individual and total isoflavones in seed from plants carrying a single mutation in IFS1 or ISF2 (IFS1 W128*; ISF2 K158N) and plants carrying double mutations in both ISF1 and ISF2 (IFS1 W128*/IFS2 K158N) compared to WT seed. The results are shown as a percentage of wild type isoflavone levels from plants grown at the same time (either 2006 or 2007). The residual content of isoflavones in seed (FIG. 6) is reduced to 20% of WT in each of the IFS1 and IFS2 single mutants and reduced to about 10% of WT in the double mutant. The residual 10% of isoflavones in the double mutant is attributed to the activity of the unmutated IFS2-2 gene in this line. Creating lines that combine mutations in all ISF genes would further reduce isoflavone levels.

EXAMPLE 3

Evaluation of IFS1-Mutation W128* and IFS2-Mutation K158N Combined in a Double Mutant IFS1+IFS2

Plants carrying the IFS1 mutation W128* were crossed sexually with plants carrying the IFS2 mutation K158N using IFS1 mutants as pollen donors. The F2 segregating seedlings were genotyped and selected for the presence of both IFS1 mutation W128* and IFS2 mutation K158N. Isoflavone content of F3 seeds from selected F2 plants was determined as described above under "Isoflavone Content".

TABLE 5

Isoflavone Content of a Double Mutant (IFS1 + IFS2) (μg/kg)

| | Daidzin | Glycitin | Genistin | Daizein | Glycitein | Genistein | Total |
|---|---|---|---|---|---|---|---|
| WT834-fall 2007 | 993.5 | 316.5 | 1165.4 | 14.9 | 233.4 | 57.4 | 2781.1 |
| DM (IFS1 + IFS2) | 48.4 | 125.9 | 85.4 | 22.3 | 0.0 | 74.9 | 356.7 |

Total isoflavone levels in seeds from soybean plants carrying both the W128* mutation in ISF1 and the K158N mutation in IFS 2 were reduced to approximately 12.8% of wild type levels. The greatest percent reductions were seen in daidzin (approximately 4.9% of wild type) and genistin (approximately 7.3% of wild type).

The above examples are provided to illustrate the invention but not to limit its scope. Other variants of the invention will be readily apparent to one of ordinary skill in the art and are encompassed by the appended claims and all their equivalents. All publications, patents, and patent applications cited herein are hereby incorporated by reference.

We claim:

1. A non-naturally occurring soybean plant that produces seeds having a reduced isoflavone level, wherein said reduced isoflavone level is a) less than 60% of the level relative to seeds from a wild type plant; and b) caused by a human-induced non-transgenic mutation in one or more isoflavone synthase genes, wherein said human-induced non-transgenic mutation is associated with a change selected from the group consisting of: a change from a tryptophan to a stop codon at amino acid 128 numbered according to SEQ ID NO: 3, a change from a lysine to an asparagine at amino acid 158 numbered according to SEQ ID NO: 4, and a change from a tryptophan to a stop codon at amino acid 315 numbered according to SEQ ID NO: 4.

2. The non-naturally occurring soybean plant of claim 1, wherein said isoflavone level is less than 55%, 50%, 45%, 40%, 35%, 30%, 25%, 20%, 15%, 5%, relative to the level in seeds from a wild type plant.

3. The non-naturally occurring soybean plant of claim 1, wherein said isoflavone level is selected from the group consisting of daidzin level, genistin level, glycitin level, daidzein level, genistein level, and glycitein level.

4. The non-naturally occurring soybean plant of claim 1, wherein said human-induced non-transgenic mutation in one or more isoflavone synthase genes is associated with a change from a tryptophan to a stop codon at amino acid 128 numbered according to SEQ ID NO: 3.

5. The non-naturally occurring soybean plant of claim 4, wherein said human-induced non-transgenic mutation in one or more isoflavone synthase genes comprises a G to A substitution at nucleotide 450 numbered according to SEQ ID NO: 1.

6. The non-naturally occurring soybean plant of claim 1, wherein said human-induced non-transgenic mutation in one or more isoflavone synthase genes is associated with a change from a lysine to an asparagine at amino acid 158 numbered according to SEQ ID NO: 4.

7. The non-naturally occurring soybean plant of claim 6, wherein said human-induced non-transgenic mutation comprises a G to T substitution at nucleotide 450 numbered according to SEQ ID NO: 2.

8. The non-naturally occurring soybean plant of claim 1 wherein said human-induced non-transgenic mutation in one or more isoflavone synthase genes is associated with a change from a tryptophan to a stop mutation at amino acid 315 numbered according to SEQ ID NO: 4.

9. The non-naturally occurring soybean plant of claim 8, wherein said human-induced non-transgenic mutation in one or more isoflavone synthase genes comprises a G to A substitution at nucleotide 1132 numbered according to SEQ ID NO: 2.

10. A non-naturally occurring soybean plant comprising human-induced non-transgenic mutations in isoflavone synthase genes that result in a change from a tryptophan to a stop mutation at amino acid 128 numbered according to SEQ ID NO: 3 and a change from a lysine to an asparagine at amino acid 158 numbered according to SEQ ID NO: 4.

11. Soybean seed, pollen, plant parts or progeny of the soybean plant of claim 1, wherein said seed, pollen, plant parts or progeny comprises said human-induced non-transgenic mutation in one or more isoflavone synthase genes.

12. Soybean seed, pollen, plant parts or progeny of the soybean plant of claim 10, wherein said seed, pollen, plant parts or progeny comprises said human-induced non-transgenic mutation in one or more isoflavone synthase genes.

* * * * *